United States Patent [19]

Hornke et al.

[11] 4,153,697

[45] May 8, 1979

[54] 8-AMINO-2-METHYL-4-PHENYL-1,2,3,4-TETRAHYDROISOQUINOLINE-8-N-GLUCURONIDE PHARMACEUTICAL PREPARATIONS AND METHOD OF USE

[75] Inventors: Ingolf Hornke, Bremthal; Hans-Wolfram Fehlhaber, Hofheim Michael Uihlein, Kriftel, all of Fed. Rep. of Germany

[73] Assignee: Hoechst Aktiengesellschaft, Frankfurt am Main, Fed. Rep. of Germany

[21] Appl. No.: 908,775

[22] Filed: May 23, 1978

[30] Foreign Application Priority Data

May 25, 1977 [DE] Fed. Rep. of Germany ....... 2723524

[51] Int. Cl.² .................... A61K 31/47; C07D 407/12
[52] U.S. Cl. ...................................... 424/258; 536/53

[58] Field of Search .................. 260/287 D; 424/258

[56] References Cited

U.S. PATENT DOCUMENTS 3,577,424  5/1971  Ehrhart et al. .................. 260/287 D

OTHER PUBLICATIONS

Chemical Abstracts, 8th Collective Index, 138785, "Glucuronides".

*Primary Examiner*—Donald G. Daus
*Assistant Examiner*—David E. Wheeler
*Attorney, Agent, or Firm*—Curtis, Morris & Safford

[57] ABSTRACT

8-Amino-2-methyl-4-phenyl-1,2,3,4-tetrahydroisoquinoline-8-N-glucuronide and its preparation as well as its use in medicaments, especially for the treatment of psychic disorders, are described.

4 Claims, 1 Drawing Figure

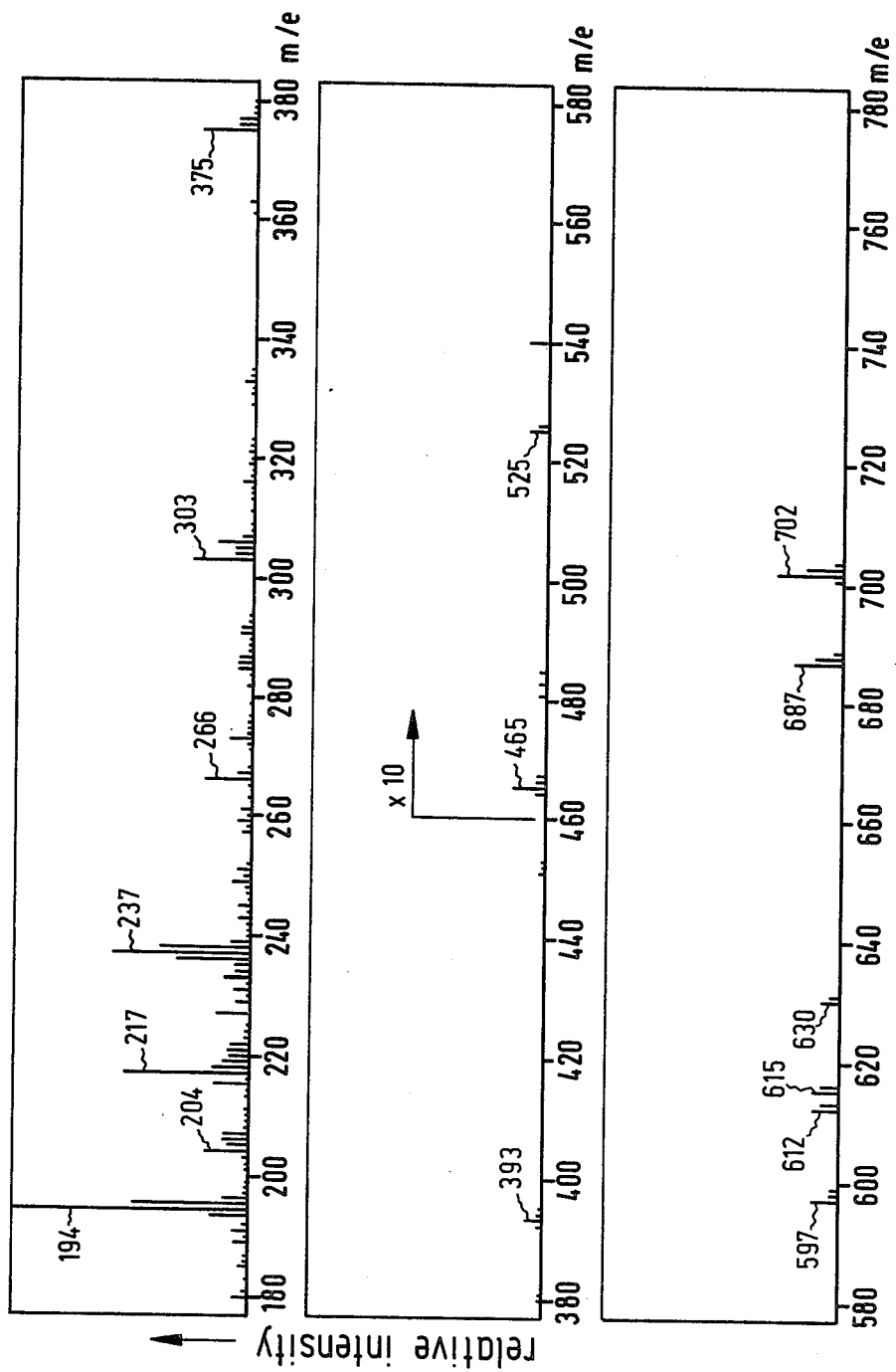

8-AMINO-2-METHYL-4-PHENYL-1,2,3,4-TETRAHYDROISOQUINOLINE-8-N-GLUCURONIDE PHARMACEUTICAL PREPARATIONS AND METHOD OF USE

The present invention relates to 8-amino-2-methyl-4-phenyl-1,2,3,4-tetrahydroisoquinoline-8-N-glucuronide and a process for its preparation.

It has already been known that the psychopharmacological agent 8-amino-2-methyl-4-phenyl-1,2,3,4-tetrahydroisoquinoline is present in the body in the form of a conjugated compound (I. Hornke et al., paper "Pharmakokinetik und Metabolismus von Nomifensin", Alival(R)-Symposium, Berlin. Oct. 1 and 2, 1976). We have now found that more than 95% of 8-amino-2-methyl-4-phenyl-1,2-3,4-tetrahydroisoquinoline is present in the body as the 8-N-glucuronide, and that about 70% thereof are excreted with the urine, from which the compound can be isolated.

Unlike the starting compound, the glucuronide is very well soluble in water and represents the actual active form. It permits the preparation of a dosage form that is appropriate for administration to the human body. The daily dose is about 10 mg per patient.

The subject of the present invention is 8-amino-2-methyl-4-phenyl-1,2,3,4-tetrahydroisoquinoline-8-N-glucuronide as well as a process for its preparation.

For preparing the above compound, alkalized urine of animals or humans to whom the starting compound has been administered, is concentrated, preferably freeze-dried, extracted with a polar solvent, for example an alcohol, preferably ammoniacal methanol, and preferably concentrated under an ammonia current. The alcoholic solution is fractionated by chromatography, preferably by way of a column charged with Amberlite(R)XAD-2 (non-specific adsorbing resin on a polystyrene basis, with a high porosity, Rohm & Haas, USA), the elution being effected with mixtures of water and an alcohol, for example methanol, with an increasing alcohol content. The pH value of the eluting agent is adjusted to about 8, for example with ammonia. From the fractions containing the conjugated compound, the glucuronide is extracted after concentration, preferably under an ammonia current, by further chromatography, for example by thin-layer chromatography according to the "line elution technique" on silica gel plates. As the eluant there may be used, for example, a mixture of isopropanol, n-butylacetate, water and concentrated ammonia in the ratio of 10:6:3:1 (V:V:V:V).

With this mixture and the use of silica gel plates of Macherey & Nagel Sil G $UV_{254}$, a $R_f$ value of 0.22 is found at room temperature.

The product was identified by interpretation of the highly resolved mass spectrum (see FIG. 1) as 8-amino-2-methyl-4-phenyl-1,2,3,4-tetrahydroisoquinoline-8-N-glucuronide, after having been reacted before with N-methyl-N-trimethylsilyltrifluoroacetamide. This result was confirmed by way of gas and thin-layer chromatography.

The product is well soluble in water and stable at a pH value of more than 7.2. The glucuronide may be brought into a therapeutically suitable form, by means of the usual carriers and/or additives, to be used as a medicament.

The following scheme has been indicated as an Example for the preparation of the glucuronide.

The figure shows the mass spectrum of the silylated glucuronide.

Scheme

```
                          urine
pH                        + NH4OH dilut. to 8.5
lyophilisation            − H2O          ...9
extraction                2 × with 150 ml of methanol/NH4OH
centrifugation            conc. 1.000/5 per 200 ml of urine
                          (starting volume)

φ ← sediment           supernatant
  rotary eva-             − methanol
  porator (NH3)           + 100 ml of H2O
  dissolve                  (ammoniacal pH 8 ...9
        XAD-2 fractination elution with ammoniacal
  (preliminary elution     water/methanol mixtures
  with ammoniacal H2O      pH 8 ...9
  pH 8 ...9)
```

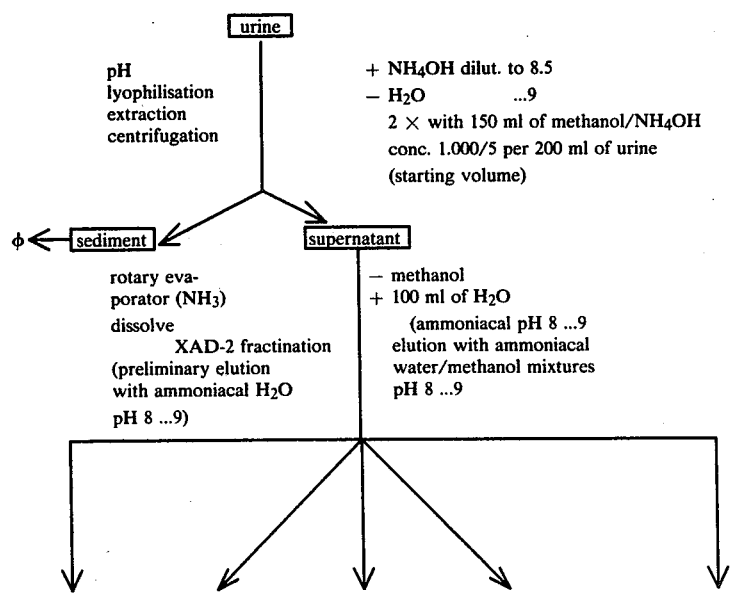

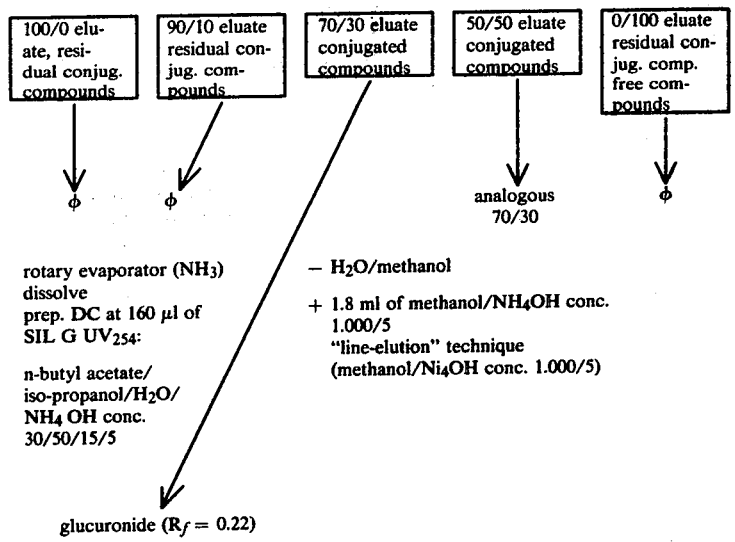

We claim:

1. 8-Amino-2-methyl-4-phenyl-1,2,3,4-tetrahydroisoquinoline-8-N-glucuronide.

2. A pharmaceutical composition for the treatment of psychic disorders comprising an effective amount of a compound as in claim 1 in combination with a pharmaceutically acceptable carrier therefor.

3. The method of treating psychic disorders in a patient suffering therefrom which comprises administering to said patient an effective amount of a compound as in claim 1.

4. A method as in claim 3 wherein about 10 mg of said compound are administered daily.